(12) United States Patent
Figovsky et al.

(10) Patent No.: US 7,232,877 B2
(45) Date of Patent: Jun. 19, 2007

(54) PREPARATION OF OLIGOMERIC CYCLOCARBONATES AND THEIR USE IN IONISOCYANATE OR HYBRID NONISOCYANATE POLYURETHANES

(75) Inventors: Oleg Figovsky, Haifa (IL); Leonid Shapovalov, Haifa (IL)

(73) Assignee: Homecom Communications, Inc., Ridgefield, CT (US)

( * ) Notice: Subject to any disclaimer, the term of this patent is extended or adjusted under 35 U.S.C. 154(b) by 0 days.

(21) Appl. No.: 10/491,268

(22) PCT Filed: Oct. 1, 2002

(86) PCT No.: PCT/US02/31120

§ 371 (c)(1),
(2), (4) Date: Mar. 29, 2004

(87) PCT Pub. No.: WO03/028644

PCT Pub. Date: Apr. 10, 2003

(65) Prior Publication Data

US 2004/0192803 A1 Sep. 30, 2004

(51) Int. Cl.
*C08G 64/00* (2006.01)
(52) U.S. Cl. ............. 528/196; 521/155; 521/178; 528/198; 528/421

(58) Field of Classification Search ............ 521/155, 521/178; 528/196, 198, 421
See application file for complete search history.

(56) References Cited

U.S. PATENT DOCUMENTS

| 1,417,883 | A | | 5/1922 | Beers | |
|---|---|---|---|---|---|
| 5,175,231 | A | * | 12/1992 | Rappoport et al. | 528/106 |
| 5,506,363 | A | * | 4/1996 | Grate et al. | 568/401 |
| 5,786,435 | A | * | 7/1998 | Marutani et al. | 526/273 |
| 6,120,905 | A | * | 9/2000 | Figovsky | 428/425.6 |
| 2001/0008924 | A1 | | 7/2001 | Rappoport | |

FOREIGN PATENT DOCUMENTS

JP 05202022 * 8/1993

\* cited by examiner

*Primary Examiner*—Terressa Boykin
(74) *Attorney, Agent, or Firm*—Kirschstein, et al.

(57) ABSTRACT

A method and apparatus for synthesis of oligomeric cyclocarbonates from epoxy compounds and carbon dioxide in the presence of a catalyst. Star epoxy compounds and their preparation and use in making star cyclocarbonates, star hydroxy urethane oligomers, and star NIPU and HNIPU. Acrylic epoxy compounds, acrylic cyclocarbonates, acrylic hydroxy urethane oligomers, and acrylic NIPU and HNIPU and their methods of preparation.

26 Claims, 6 Drawing Sheets

Fig. 7

| Examples | The Catalyst % | Technological Data | | | Initial Epoxy Compounds | Conversion % |
|---|---|---|---|---|---|---|
| | | Time Minutes | P Bar | T°C | | |
| 1 | Tetrabutylammonium Bromide (C₄H₉)₄NBr  0.5% | 45 | 8 | 70-120 | Epoxy resin D.E.R.-324 | 99 |
| 2 | Tetrabutylammonium Bromide (C₄H₉)₄NBr  0.5% | 40 | 8 | 70-120 | Epoxy resin Oksilin-6B | 99 |
| 3 | Tetrabutylammonium Bromide (C₄H₉)₄NBr  0.5% | 90 | 8 | 70-120 | Epoxy resin D.E.N.-431 | 97 |
| 4 | Tetrabutylammonium Iodide (C₄H₉)₄NI  0.5% | 40 | 1.5 | 70-120 | Epoxy resin D.E.R.-324 | 98 |
| 5 | Tetrabutylammonium Chloride (C₄H₉)₄NCl  0.5% | 120 | AP | 70-120 | Epoxy resin D.E.R.-324 | 98 |
| 6 | Tetrabutylammonium Bromide (C₄H₉)₄NBr  0.5% | 90 | 1.5 | 70-120 | Epoxy resin Laproxide | 98 |
| US Patent No. 51752312 | Tetrabutylammonium Bromide (C₄H₉)₄NBr  0.5% | 180 | 10 | 130 | Epoxy resin D.E.R.-324 | 97 |

Fig. 8

| Examples | Control | 7 | 8 | US Patent No. 5175231 | 9 | 10 |
|---|---|---|---|---|---|---|
| Average functionality of olygomers: | | | | | | |
| Amine | 2 | 2 | 2 | 2 | 2 | 2 |
| "Star" AHUOIF | – | – | – | – | 4 | 4 |
| CC | 3 | – | – | 3 | – | – |
| "Star" HUOIF | – | 4 | 5 | – | 4 | 4 |
| "Star" EOIF | – | – | – | – | 4 | 4 |
| Epoxy | – | – | – | 2 | 2 | 2 |
| f average | 2.4 | 2.67 | 2.86 | 2.07 | 2.07 | 2.6 |
| Departure from Stoichoimetric Ratio of Amine Olygomer / Cyclocarbonate / Epoxy olygomer | 0.9 | 0.9 | 0.95 | 0.95 | 0.97 | 0.97 |
| Properties | | | | | | |
| Tensile strength Mpa | 0.4 | 1.3 | 0.7 | 8.0 | 11.0 | 9.0 |
| Ultimate elongation % | 110 | 250 | 300 | 50 | 90 | 120 |

PREPARATION OF OLIGOMERIC CYCLOCARBONATES AND THEIR USE IN IONISOCYANATE OR HYBRID NONISOCYANATE POLYURETHANES

FIELD OF THE INVENTION

The present invention generally relates to the preparation of oligomeric cyclocarbonates and their use in nonisocyanate polyurethanes (NIPU) and hybrid nonisocyanate polyurethanes (HNIPU). In particular, the present invention relates to an improved method of and apparatus for synthesis of oligomeric cyclocarbonates from epoxy compounds and carbon dioxide. The present invention further relates to the novel star and acrylic cyclocarbonate compounds and their use in novel star and acrylic hydroxy urethane oligomers and novel star and acrylic NIPU and HNIPU compositions.

BACKGROUND OF THE INVENTION

Nonisocyanate polyurethane materials differ completely, both in structure and in properties, from polyurethanes produced from isocyanate containing oligomers and/or starting materials.

Prior art methods of producing polyurethane compounds that rely upon the reaction of terminated hydroxyl groups with terminated isocyanate groups requires the use of toxic starting materials such as isocyanates and competing side-reactions during production generates gases that result in an undesirable highly porous material. Furthermore, polyurethanes derived from isocyanates have hydrolytically unstable chemical bond rendering them highly susceptible to environmental degradation.

These problems can be overcome by making of a polyurethane without the use of toxic isocyanates, thus creating a modified polyurethane with lower permeability and increased chemical resistance properties to aqueous solutions of acids and alkalis.

We previously discovered and disclosed in U.S. Pat. No. 6,120,905 to Figovsky, the structure of hybrid nonisocyanate polyurethane network polymers, composite formed therefrom, and their synthesis. These polyurethanes are formed by a reaction of cyclocarbonates with primary amine polyfunctional oligomers. Our prior patented process carries out the cyclocarbonate-oligomer synthesis in thin film reactor at a temperature of 65 to 105° C., and at the pressure of about 6.0 to 8.5 atm for about 190 to 330 minutes. The resultant product contains not only terminated cyclocarbonate-groups but also terminated epoxy groups. We have subsequently found this process to have a very small capacity and yields cyclocarbonate-oligomer with yellow color, which is not suitable for use with clear coats and other products requiring a clear or white color.

Urethane oligomers can be prepared, as shown in U.S. Pat. No. 5,175,231 to Rappoport et al., by reacting a compound containing a plurality of cyclocarbonate groups with a diamine where the amine groups have different reactivities with cyclocarbonate, so as to form urethane oligomer with amine terminated groups. The amino-oligomer is used as a hardener of epoxy resin and can be cross-linked by reacting it with an epoxy resin to form a network structure. The cyclocarbonates are synthesized from epoxy resins and carbon dioxide in the presence of catalyst in a reactor under pressure 130-150 psi (8.9-10.3 bar) and elevated temperature 240° F. (150° C.). In the Rappoport et al. process, carbon dioxide is introduced in the bottom of the reactor previously loaded with epoxy compound and catalyst. The conversion of epoxy groups to cyclocarbonate groups is strongly dependent upon the saturation of the epoxy compound by the carbon dioxide. In the Rappoport et al process, despite vigorous stirring that generates a foam, the reaction still takes several hours and requires the use of high temperatures, high pressures, large amounts of catalyst and long reaction times, to avoid having a significant amount of unreacted epoxy groups that reduce the concentration of the urethane groups and the number of hydrogenated links in the final polyurethane network. Unfortunately, although Rappoport et al. are able to ensure that nearly all the epoxy groups have been turned into cyclocarbonate groups in this reaction, they also end up producing undesirable side reactions and products, while being more expensive and time-consuming.

Other efforts to create such nonisocyanate polyurethanes have had further problems. U.S. Pat. No. 4,758,615 to Engel Dieter, et al. discloses the process of synthesis of polymers containing nonisocyanate urethane groups by reacting polyamino compounds with polycarbonates and reacting the reaction product further with polycarboxylic acids for preparing aqueous polymer dispersions.

Production of other nonisocyanate polyurethanes based on the reaction between the oligomeric bifunctional cyclocarbonate oligomers and amines are disclosed by U.S. Pat. No. 5,340,889 to Crawford et al. In this process, liquid hydroxyurethane products are prepared by reacting a molar excess of bis-carbonate of a bis-glycidyl ether of neopentyl glycol or 1,4-cyclo-hexanedimenthanol with polyoxyalkylenediamine. However, the resultant polyurethanes lack a cross-linked network structure, and thus are not chemically resistant and also are not suitable for construction and structural materials.

The reaction of cyclocarbonates with amine compounds can result in products other than polyurethanes. For example, USSR Inventors Certificate No. 1353792 to Danilova, et al. discloses reacting an epoxy-cyclocarbonate resin, urea formaldehyde, triazine resin and amine hardener to prepare an adhesive composition. And U.S. Pat. No. 4,585,566 to Wollenberg discloses the process of synthesis of dispersants by reaction of a primary or secondary amino group with mono-cyclic carbonate.

The tensile strength and deformation properties of nonisocyante polyurethanes are comparable with standard isocyanate polyurethanes, but the nonisocyanate polyurethanes do not have pores, and thus are not sensitive to moisture in the surrounding environment. The main properties of nonisocyanate polyurethanes depend on the structure and the functionality of the cyclocarbonate and amine oligomers from which it is made.

As noted above, the known reactions for preparing nonisocyanate polyurethanes by using cyclocarbonates and primary amines are problematic in that the reaction stops before the process is completed resulting in an incompletely hardened network polymer that adversely affects the properties of network polymer. Although attempts have been made to prepare and add hardeners for epoxy resin, such as shown in U.S. Pat. No. 5,175,231, they have not is been successful in increasing the desirable properties of the nonisocyanate polyurethanes.

The preparation of cyclocarbonates has also been fraught with difficulties and products unsuitable for use in further processing into nonisocyanate polyurethanes. For example the process disclosed in U.S. Pat. No. 5,817,838 to Gründler et al. prepares cyclocarbonates from epoxides and carbon dioxide in the presence of a quanternary ammonium or phosphonium salt with a further silver salt catalyst to assist the reaction process. However, the use of the silver salt catalyst results in a material that is unacceptably dark in color.

Other processes for the preparation of cyclocarbonates require the use of high reactor temperatures despite the use of various types of catalysts. For example, U.S. Pat. No. 5,153,333 uses quaternary phosphonium compounds as a catalyst, but still requires reactor temperatures of 200° C. U.S. Pat. No. 4,835,289 uses alkali iodides and reactor temperatures of 180° C.

SUMMARY OF THE INVENTION

The present invention is directed to an improved method of synthesis of oligomeric cyclocarbonates from digomeric epoxides and carbon dioxide in the presence of a catalyst in a reactor or cascade of reactors and the apparatus therefore. The improved method allows the reaction to progress to completion at low temperatures and low pressures for short time periods without side reactions and the production of byproducts.

The invention is further directed to NIPU and HNIPU with improved properties and the compositions from which they are produced.

In particular, the invention is directed to a highly functionalized star epoxy compounds, star cyclocarbonates, star hydroxy urethane oligomers, and star NIPU and HNIPU, as well as to and their method of preparation.

The present invention is also directed to an acrylic epoxy compounds, an acrylic polymer with pendant cyclocarbonate groups, an acrylic backbone hydroxy urethane oligomers, and acrylic backbone NIPU and HNIPU and their methods of preparation.

BRIEF DESCRIPTION OF THE DRAWINGS

FIG. 7 is a Table showing the results of Examples 1-6 as compared to the prior art;

FIG. 8 is a Table showing the network polyurethane properties of Examples 7-9 relative to a control and to the prior art.

DETAILED DESCRIPTION OF THE INVENTION

The synthesis of nonisocyanate network polyurethanes and hybrid nonisocyanate network polymers involves a number of stages. The first stage is the preparation of a cyclocarbonate from the reaction of an epoxy or epoxide with carbon dioxide. The resultant cyclocarbonate is reacted with an amine containing compound to form an hydroxy urethane oligomer. The hydroxy urethane oligomer is then cross linked to form a nonisocyanate network polyurethane (NIPU) or a hybrid nonisocyanate network polyurethane (HNIPU). The properties of the resultant NIPU or HNIPU depend upon the properties of the cyclocarbonate and amine oligomers from which it is produced.

Others in the art have had problems with obtaining NIPU and HNIPU with the desired properties due to many factors, including the problems with obtaining a cyclocarbonate material of sufficient purity.

Accordingly, the present invention is directed to an improved method and apparatus for the preparation of cyclocarbonates from epoxides and epoxy containing compounds by reaction with carbon dioxide. The invention is further directed to the preparation of novel highly functionalized star cyclocarbonate and novel acrylic backbone polymers with pendant cyclocarbonate groups and the use of such novel compounds in the preparation of novel hydroxy urethane oligomers and novel NIPU and HNIPU compositions.

In prior reaction systems, as described above, carbon dioxide is introduced into the bottom of a reactor vessel and reacts with the epoxide as it upwardly traverses the reaction mass. To ensure that the reaction proceeds, it is necessary to use high pressures of carbon dioxide, as well as high temperatures, long reaction times, and catalysts. All of these degrade the resultant product requiring separation and purification steps before the cyclocarbonate product can be used.

The improved process of the present invention utilizes a reactor that maximizes the surface contact area between the reactionary epoxide mass and the carbon dioxide, thus obviating the need for high temperatures, high pressures, and long reaction times. In the process of the present invention, the saturation of reaction mass by carbon dioxide is maximized by both feeding the carbon dioxide to the head space above the reaction mixture and feeding the carbon dioxide directly into the reaction mass by means of a turbine mixing device with a gas entrainment impeller.

Figure 1A:
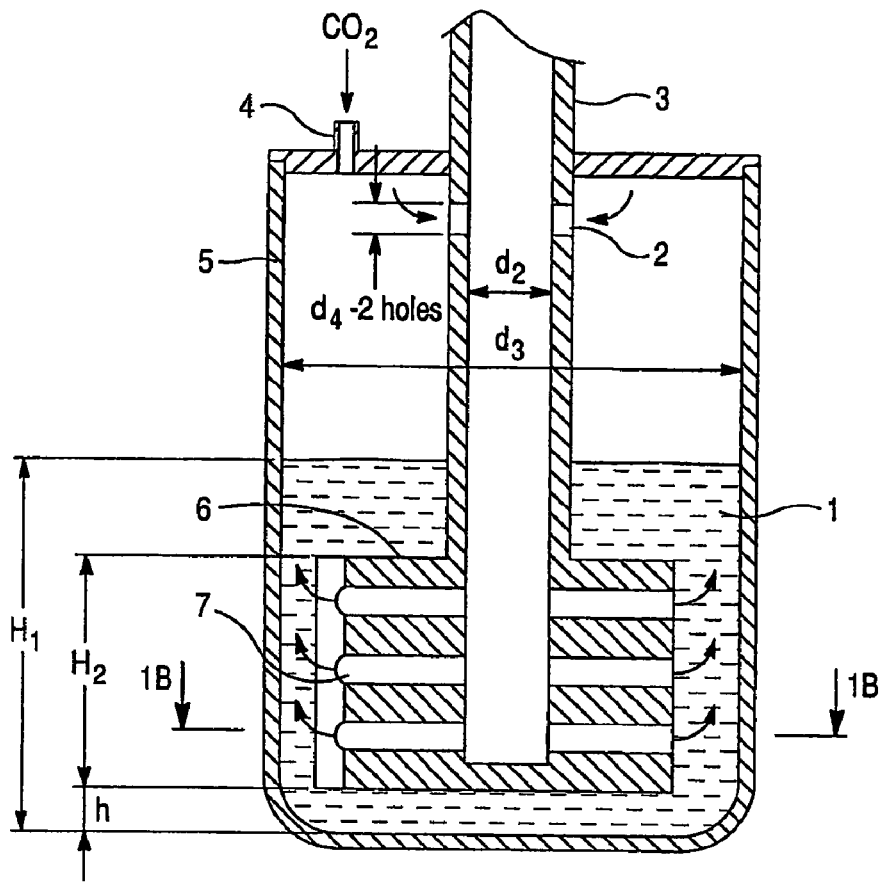
FIG. 1A is a schematic representation of a turbine mixing device reactor in which the improved method of the present invention is conducted.

The process can best be understood by reference to FIG. 1A, which shows a reaction vessel 5 having a diameter $d_3$ in which the epoxide is charged to form reaction mass 1 having a height $H_1$. Carbon dioxide is introduced by means of inlet 4 into the head space above the reaction mixture 1. Carbon dioxide is also fed by means of a gas turbine mixer which comprising a hollow shaft 3 in fluid communication with hollow gas entrainment impeller 6 that feed the carbon dioxide by means of gas outlets 7 directly into the reaction mixture 1 while rotating. The hollow shaft 3 has an inside diameter of $d_2$ and contains inlet ports of openings 2, each with a diameter of $d_4$, that permit the carbon dioxide gas to continuously recirculate from the head space above the reaction mass 1 directly into the reaction mass 1. The carbon dioxide gas enters near the top of the hollow shaft 3 through openings 2 and is drawn through the hollow shaft 3 and through hollow gas entrainment impeller 6 having a height $H_2$ and is then the expelled through dispersion ports or outlets 7 located at the tip of the impeller 6. The dispersion ports or outlets each have a diameter of $d_5$. The diameter of the impeller 6, as measured from tip to tip, is denoted by $d_1$. The impeller is located a distance h from the bottom of the reactor 5. The rotation of the impeller 6 creates a vacuum at the tip of impeller where the dispersion ports or outlets 7 are located. The speed of rotation is directly related to the vacuum created, and thus the driving force for the dispersion of the carbon dioxide gas into the reaction mass 1, with the higher the speed, the higher the vacuum, and the higher the driving force.

Figure 1B:
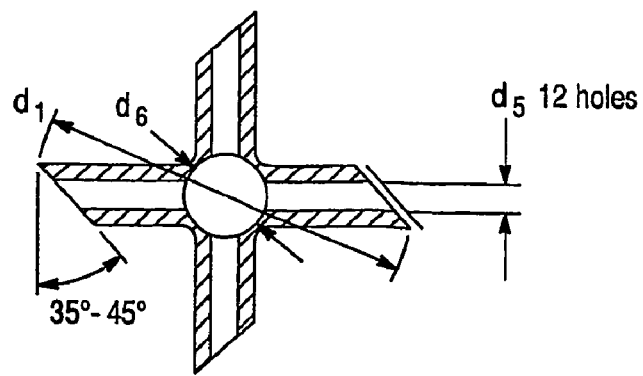
FIG. 1B is a cross section of the turbine mixer blade of FIG. 1 taken on line 1B.

In a preferred embodiment of the invention, the ratio of the inside diameter $d_2$ of shaft 3 to the largest diameter $d_1$ of the turbine mixing device measured from tip of impeller to tip of impeller as shown in FIG. 1B is preferably in the range of about 1:4 to about 1:6, with a range of 1:4 the most preferred.

In another preferred embodiment, the ratio of the sum of the square of the diameter $d_4$ of the inlet ports 2 on the hollow shaft 3 to the sum of the square of outlet ports $d_5$ as shown in FIG. 1B is preferably from about 1:3 to about 1:4. ($\Sigma d_4 : \Sigma d_5$ FIG. 1).

In yet another preferred embodiment of the invention, the ratio of the height $H_2$ of impeller 7 to the height $H_1$ of mixing layer or reaction mass 1 is preferably from about 1:2 to about 1:4.

The synthesis of cyclocarbonates can be carried out in a single reactor in a batch wise process or in a series or cascade of reactors on a continuous action basis. When a cascade of reactors is used, a cyclocarbonate product of extremely great purity can be obtained.

The reaction is conducted in the presence of a suitable catalyst, which are well-known to those of skill in the art, and include quaternary ammonium salts, quaternary phosphonium salts, quaternary arseniurm salts, alkali metal halides of Cl, Br, I, and the like.

The reaction is preferably conducted at a temperature of about 70-180° C. and a pressure of at least one atmosphere, preferably from about 1-15 bar. For a clearer product, lower temperatures are preferred.

This reaction system has unexpectedly been found to have excellent gas-liquid contact without the generation of foam. Furthermore, due to the excellent gas-liquid contact made in this reactor, the reaction time is greatly reduced, generally by a factor of 2 to 4, over other known systems. For example, under identical conditions of temperature and pressure, the present system requires only 40 to 120 minutes for reaction, while that shown in U.S. Pat. No. 5,175,231 requires at least a time period of 180 minutes.

We have also found that this reaction system permits a gentle reaction without the use of harsh conditions that result in the production of undesired byproducts and side reactions.

The present invention further relates to the preparation of novel network nonisocyanate polyurethanes using the novel synthesized cyclocarbonates of the present invention. In one embodiment of the invention, the novel synthesized cyclocarbonates are star carbonates of increased functionality. In another embodiment, the novel synthesized cyclocarbonates are acrylic polymers with pendant cyclocarbonate groups.

Figure 5:
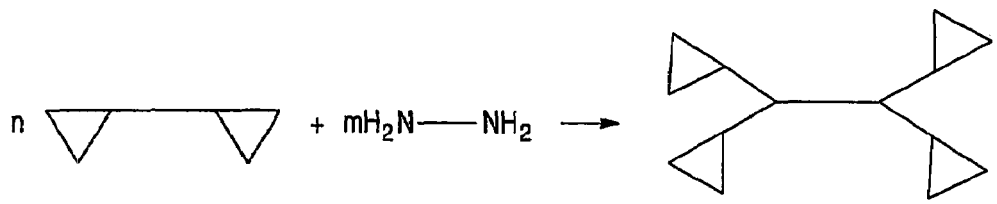
FIG. 5 is a schematic representation of another embodiment of the reaction to produce epoxy oligomer with increased functionality (EOIF)

Functionality, also referred to as "f", refers to the number of reactive centers and is calculated from the structural formula. Thus, an epoxy terminated oligomer would have two epoxy groups, and thus a functionality of 2. If it is reacted in accordance with the present invention as shown in FIG. 5, the resultant star epoxy oligomer would have a functionality of 4.

The star oligomers of the present invention refer to oligomers is with multiple functional groups that have been linked together using one functional group from each oligomer to form a linkage, such as an hydroxyurethane linkage, to form a polymer with increased functionality. This linkage process can be used to create a star polymer of any desired functionality. Generally a functionality of about 2 to about 6 is preferred, and more preferably about 3 to about 5, as too great of an increase in functionality can hinder the use of the star oligomer in preparation of desired products such as network nonisocyante polyurethanes.

For example, a star-epoxy oligomer is a product of the reaction between an oligomer with terminated epoxy groups (by functionality not less than 1.99) and amino oligomer with primary amino groups (by functionality no less than 1.99) so that one terminated epoxy group from one oligomer and one terminated epoxy group from another oligomer both react with the amino oligomer to form an hydroxyurethane linkage connecting the two epoxy oligomers together to form a star epoxy oligomer. See for example FIG. 5 which shows the reaction of 4 epoxy oligomers to form a star epoxy oligomer of functionality 4, i.e. 4 unreacted epoxy groups remaining.

Figure 2A:
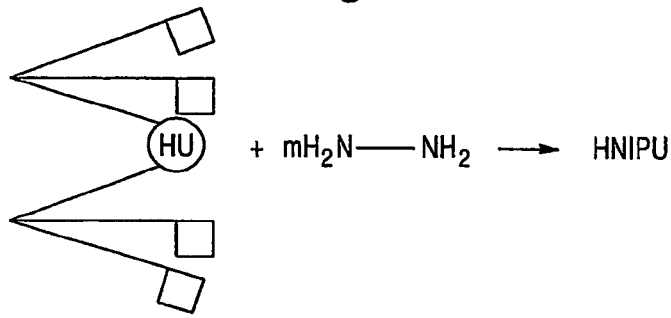
FIG. 2A is a schematic representation of one embodiment of the reaction to produce network nonisocyanate polyurethanes (NIPU)

In one embodiment of the invention, the network nonisocyanate polyurethanes (NIPU) of this invention are prepared by an improved method by interaction in situ of at least one cyclocarbonate hydroxyurethane "star" oligomer (star cyclocarbonate oligomer) with increased functionality ($f \geq 3$) and having terminated cyclocarbonate groups and at least two hydroxyurethane linkage groups with amino-oligomer containing at least two terminated primary amino groups with at least two hydroxyurethane groups. See FIG. 2A.

Figure 2B:
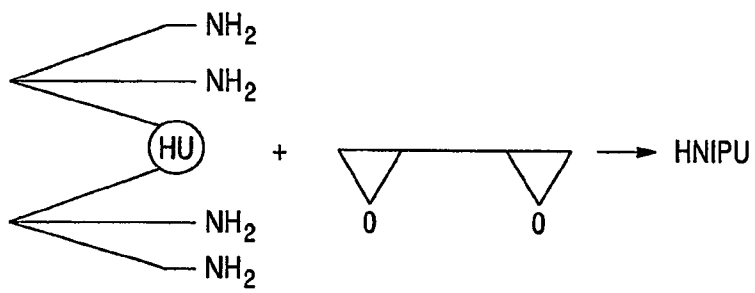
FIG. 2B is a schematic representation of another embodiment is of the reaction to produce NIPU.
Figure 3:
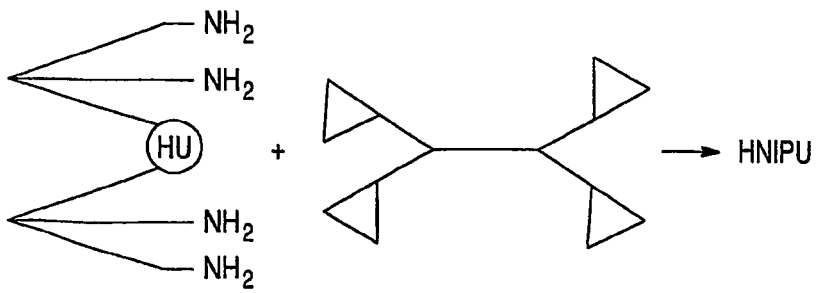
FIG. 3 is a schematic representation of an embodiment of the reaction to produce hybrid network nonisocyanate polyurethanes (HNIPU)

In another embodiment of the invention, the network nonisocyanate polyurethanes are prepared by interaction of "star" oligomer with terminated amino groups (FIG. 6) with oligomer containing epoxy groups. (functionality $f \geq 2$). The network hybrid nonisocyanate polyurethanes are prepared. See FIG. 2B.

In another embodiment of the invention, the network nonisocyanate polyurethanes are prepared by interaction of "star" oligomer with terminated amino groups (FIG. 6) and epoxy oligomer with increased functionality (EOIF) (FIG. 5).

Figure 4:
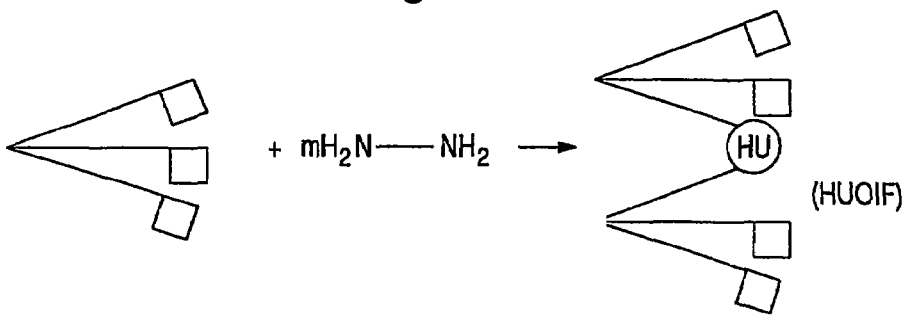
FIG. 4 is a schematic representation of an embodiment of the reaction to produce hydroxyurethane oligomer with increased functionality (HUOIF)

In another embodiment of the invention, "star" hydroxyurethane oligomer with increased functionality (HUOIF) is synthesized by reacting n moles of oligomer, containing terminated cyclocarbonate groups (functionality $\geq 3$), and m moles of amines, wherein n>m. See FIG. 4.

In another embodiment of the invention, "star" hydroxyurethane oligomer with increased functionality (HUOIF) is synthesized by reacting n moles of oligomer, containing terminated cyclocarbonate groups (functionality $\geq 3$), and m moles of amines, where n>m. See FIG. 5.

In another embodiment of the invention, "star" hydroxylamino oligomer with increased functionality (AHUOIF) with terminated amino groups is synthesized by interaction of n moles of HUOIF (functionality $f \geq 3$) and m moles of primary diamines where $m \geq f$. See FIG. 6.

In a further embodiment of the invention, the star polymers are multi or polyfunctional polymers can contain a multiplicity of different types of functional groups. For example, the star epoxy oligomer may have epoxy, cyclocarbonate, amine and other groups, not just the epoxy groups.

In yet another embodiment of the invention, acrylic epoxies in the form of an acrylic backbone polymers with pendant epoxide groups, are used to produce novel acrylic cyclocarbonate oligomers. The novel acrylic cyclocarbonate oligomers are reacted with primary amines, diamines and tertiary amines to form a novel acrylic aminohydroxyurethane that can be cured to form an acrylic NIPU or HNIPU. Polyfunctional acrylic oligomers known to those skilled in the art can be used in the present invention. For example, copolymers of acrylic monomers methylmethacrylate, butylacrylate, 1-methacrylate-2,3-epoxy, and the like can be used. An example of such a polyfunctional acrylic oligomer is

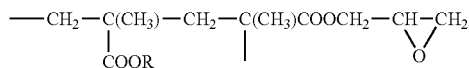

The novel star and acrylic NIPU and HNIPU compositions of the present invention can take any suitable form and the oligomers from which it is made can be selected to provide the desired properties such as gloss, degree of hardness, flexibility, UV stability, abrasion resistance, weathering resistance and the like. From this disclosure, one of skill in the art would be able to make an appropriate selection of materials without undue experimentation.

Due to their superior structure and excellent resistance to degradation, the novel star and acrylic NIPU and HNIPU compositions of the present invention are useful for numerous applications including crack resistant composite materials, chemically resistant coatings, sealants, glues, paints and the like. These novel compositions are useful in a host of industries. For example, uses in the automotive industry include bumpers, dashboards, inhibiting sealants, paints, plastics, repair putty, seating, steering wheels, trim components, truck beds, and the like. Aerospace uses include airplane and rocket sealants, interior components, seating, syntactic non-burning foam, and the like. Uses in the construction industry are myriad and include adhesives, coatings, coverings, crack barrier concrete, elastomers, epoxy resin hardeners, exterior wallboard, flooring, foams, glues, metals, plastics, plywood, rooftops, sealants, wood coatings, and the like. Industrial uses include coatings, paints and sealants for heavy industrial equipment, machinery, molded parts, and the like. The novel compositions are particularly well suited for marine environments and can be used for bridge decks, coatings, interior and exterior components, paints, sealants and the like. Other possible uses include appliances, footwear, furniture, plastics, synthetic leather, toys, and the like.

These novel compositions are particularly useful as coatings and paints and can be used as coatings on industrial machines, as floor coatings, as coatings and paints for automobiles, trucks, and buses, as coatings and paints on outdoor structures such as bridges and trusses, as coatings and paints on interior structural members such as trusses, ceilings, walls, and the like.

By selection of the oligomers used in preparation of these novel compositions, one skilled in the art can provide a liquid paint or coating composition containing these novel compositions that is sprayable with conventional paint equipment, has a potlife of sufficient time, has reduced VOC, and suitable cure times. The resultant cured coatings have a desired gloss, hardness, adhesion, impact resistance, corrosion resistance, humidity resistance, chemical resistance, and weathering resistance.

In a further embodiment of the present invention, these novel star and acrylic NIPU and HNIPU compositions can be foamed using a blowing agent such as pentane to provide a foamed coating composition.

The present invention provides structures, which solve the problem of increasing of the mechanical properties of NIPU and HNIPU.

Since the present reaction does not require the use of highly toxic materials, it is possible to perform the reaction without special equipment.

In general, the synthesis of nonisocyanate network polyurethanes of the present invention is conducted as follows:

The First Stage.

Any suitable epoxy compound known to one skilled in the art can be reacted with carbon dioxide to form the corresponding cyclocarbonates. The reaction can be conducted in either a batch-process (single reactor) or in a continuous process (cascade or series of reactors) in the presence of a suitable catalyst well-known to those of skill in the art. Examples of suitable catalysts include quaternary ammonium salts, quaternary phosphonium salts, quaternary arsenium salts, alkali metal halides (Cl, Br, I) and the like of alkali metal. In a preferred embodiment of the invention, the reactor temperature is 70-180° C. and pressure 1-15 bar is supported.

The carbon dioxide is fed to the upper part of the reactor, from which it is fed by the turbine mixing device (gas entrainment impeller) directly in to the reactionary mass.

Due to the dispersion effects of the turbine mixing device which result in a "soaking up" of the carbon dioxide by the reactionary mass, the carbon dioxide is entered into the reactionary mix throughout the entire working volume of the reactionary mass and thus raises saturation of epoxy compounds by the carbon dioxide enabling the reaction to be completed in a significantly shorter time than in the prior art devices utilizing periodic action under pressure. It provides faster and complete production of cyclocarbonate, with the reaction of the present invention being 2 to 4 times faster than that in the prior art.

EXAMPLE 1

A reactor of the type depicted in FIG. 1 is used to efficiently prepare cyclocarbonates.

500 grams of epoxy resin D.E.R.-324 (Dow Chemical) were mixed with the catalyst tetrabutylammonium bromide $(C_4H_9)_4NBr$ in quantity 0.5% of weight of epoxy and loaded into the reactor (volume—1 liter). Carbon dioxide was fed for a period of 45 minutes through the hollow shaft and out the holes at the ends of the impeller into the epoxy/catalyst mixture. The initial reactor conditions were a temperature of 70° C., and a pressure of 8 bar, at which point absorption of the carbon dioxide commenced. The reaction was exothermic, and finished at a temperature of 120° C. The mean velocity of absorption $CO_2$ during the reaction was 2.4 grams per minute.

The reaction resulted in the preparation of 580 grams of a cyclocarbonate oligomer containing 35% cyclocarbonate groups and 0.3% epoxy groups. Conversion was 99%.

EXAMPLE 2

Using the procedure of Example 1, 620 grams epoxy resin Oksilin-6B (Russia) were mixed with the catalyst tetrabutylammonium bromide $(C_4H_9)_4NBr$ in quantity 0.5% of weight of epoxy and loaded into the reactor (volume—1 liter). Carbon dioxide was fed to the reactor for a period of 40 minutes through the hollow shaft and out of the holes in the impeller into the epoxy/catalyst mixture. The initial reactor conditions were a temperature of 70° C. and a pressure of 8 bar, at which point absorption of the carbon dioxide commenced. The reaction is exothermic and at the completion thereof the temperature was 120° C. The mean velocity of absorption $CO_2$ during the reaction was 1.7 grams per minute.

The reaction resulted in the preparation of 580 grams of cyclocarbonate oligomer containing 22.7% cyclocarbonate groups and 0.1% epoxy groups. Conversion was 99%.

EXAMPLE 3

Using the procedures of Example 1, 523 grams of epoxy resin D.E.N.-431 (Dow Chemical) were mixed with the catalyst tetrabutylammonium bromide $(C_4H_9)_4NBr$ in quantity 0.5% of weight and the epoxy/catalyst mixture was loaded to the reactor (volume—1 liter). The carbon dioxide was fed to the reactor under a pressure of 8 bars for a period of 90 minutes. The initial temperature of the reactor was 70° C. and the final temperature increased to 120° C. due to the exothermic nature of the reaction. The mean velocity of absorption of $CO_2$ during the reaction was 2 grams/min.

The reaction resulted in the preparation of 590 grams of cyclocarbonate oligomer containing 28% cyclocarbonate groups and 1% epoxy groups. Conversion was 97%.

EXAMPLE 4

Using the procedure of Example 1, 516 grams of epoxy resin D.E.R.-324 (Dow Chemical) was mixed with the catalyst tetrabutylammonium iodide $(C_4H_9)_4NI$ in quantity of 0.5% of weight of epoxy. The epoxy/catalyst mixture was then loaded into the reactor (volume—1 liter). Carbon dioxide was fed to the reactor through the hollow shaft and out of the impeller at a pressure of 1.5 bar for a period of 40 minutes. The initial temperature of the reactants was 70° C. and increased due to the exothermic nature of the reaction to a final temperature of 120° C. The mean velocity of absorption $CO_2$ during the reaction was 2.8 grams/min.

The reaction resulted in the preparation of 580 grams of cyclocarbonate oligomer containing 34% cyclocarbonate groups and 0.5% epoxy groups. Conversion was 98%.

EXAMPLE 5

Using the procedure of Example 1, 516 grams of epoxy resin D.E.R.-324 (Dow Chemical) were mixed with the catalyst tetrabutylammonium chloride $(C_4H_9)_4NCl$ in quantity 0.5% of weight of epoxy. The epoxy/catalyst mixture was then loaded into the reactor (volume—1 liter). Carbon dioxide was fed to the reactor at atmospheric pressure for a period of 120 minutes. The initial reactor temperature was 70° C. increased to 120° C. due to the exothermic nature of the reaction.

The reaction resulted in the preparation of 500 grams of cyclocarbonate oligomer containing 34% cyclocarbonate groups and 0.3% epoxy groups. Conversion was 98%.

EXAMPLE 6

Using the procedure of Example 1, 600 grams of epoxy resin Laproxide (Russia) were mixed with the catalyst tetrabutylammonium bromide $(C_4H_9)_4NBr$ in the quantity 0.5% of weight of epoxy. The epoxy/catalyst mixture was then loaded into the reactor (volume—1 liter). Carbon dioxide was fed to the reactor at a pressure of 1.5 bar for a period of 90 minutes. The initial temperature of the reactor was 70° C. and increased to a final temperature of 120° C. due to the exothermic nature of the reaction.

The reaction resulted in the preparation of 665 grams of cyclocarbonate oligomer containing 23% cyclocarbonate groups and 0.3% epoxy groups. Conversion was 98%.

The conversion rates and reaction information of examples 1-6 are summarized in the Table of FIG. 7 and compared with the results obtained using the procedures set forth in U.S. Pat. No. 5,175,312.

Network nonisocyanate polyurethanes were prepared using the synthesized cyclocarbonates.

The Second Stage.

Figure 6:
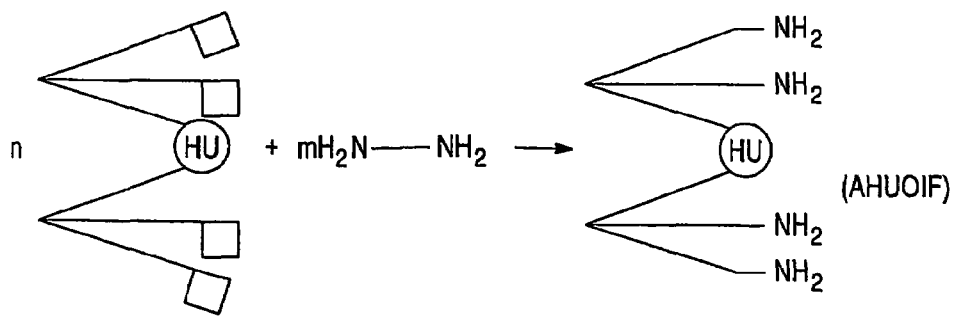
FIG. 6 is a schematic representation of another embodiment of the reaction to produce aminohydroxyurethane oligomer with increased functionality (AHUOIF)

In the second stage of the reactor, a cyclocarbonate or an epoxy is oligomer is reacted with amino containing compound, in particular a compound containing terminated amino groups, to form "star" hydroxyurethane or epoxy oligomers with increased functionality (FIG. 5-7).

Suitable terminated amino groups are those containing primary amino groups, i.e. —$NH_2$ groups without radicals. In particular, polyfunctional primary amino-terminated oligomers of the following formula may be used:

wherein
R is aliphatic, cycloaliphatic, ether, ester and acrylic groups, and
m is $\geq 3$.

Any cyclocarbonate or epoxy oligomer can be used in this reaction. In a preferred embodiment of the invention, the cyclocarbonate and epoxy oligomers are cyclocarbonate or epoxy oligomers of increased functionality having at least two and preferably more functional groups in their structure. In a preferred embodiment of the invention, the functionality is from about 3 to about 5, and is more preferably from about 3 to about 4.

In one embodiment of the invention, a cyclocarbonate oligomer with three terminal cyclocarbonate groups reacts with primary diamine as shown on the FIG. 5 to form "star" oligomer with four or more cyclocarbonate and hydroxyurethane groups. The oligomer with two terminated epoxy groups reacts with primary diamine as shown on the FIG. 6 to form "star" oligomer with four or more epoxy groups. On the base of "star" oligomers with increased functionality amino adducts were prepared (FIG. 7).

The diamines used in the present invention have amine groups with equal or different reactivities. The oligomer with increased functionality has at least average three amino groups.

The Third Stage.

The resulting urethane containing "star" oligomer can serve as a hardener for oligomers with epoxy or cyclocarbonate groups. Or "star" oligomer with terminated cyclocarbonate groups which may be cured by primary amino oligomer (f>, =2). So we have a material (the urethane containing "star" oligomers with amino end groups, cyclocarbonate end groups and epoxy end groups with increased functionality) that, have the substantial advantages over the prior art it has the increased strength and elasticity.

Any cyclocarbonate or epoxy oligomer may be used.

The practical applications of this invention are very interesting. For example, we can produce paints, adhesives, composite compounds, etc.

The present invention provides a material that has combination is of all the advantage of known nonisocyanate materials plus increased mechanical properties of polyurethane.

EXAMPLE 7

Stage II

"Star" cyclocarbonate oligomer containing hydroxyurethane groups with increased functionality was prepared by dissolving of 2M (2268 g) of cyclocarbonate oligomer Laprolat-803(Example 6) in 1M (170 g) of Isophorondiamine (CREANOVA spezialchemie GmbH). This 2438 g were charged into the reactor, which is jacketed for temperature control. The reactor was operated at atmospheric pressure and in several small portions, because the reaction is exothermic. The reaction is going at 80° C. during 3-4 hours.

It is also possible to prepare oligomers in presence of solvents. It is possible to use any of diamine and cyclocarbonate compound. After all the amine was added to the reactor samples were taken and measured for amine group concentration. The content of amine group in the finished product was about 0%, indicating that amine groups had reacted with cyclocarbonate groups and we have now new "star" hydroxyurethane oligomer with increased functionality (HUOIF).

Stage III

The urethane containing "star" oligomer from the stage I was reacted with Isophorondiamine (ISPhDA) and resulted in the formation of an elastomer with a tensile strength 1.5 Mpa and an elongation at break of 250% as measured by ASTM D638884.

EXAMPLE 8

Stage II

"Star" cyclocarbonate oligomer with increased functionality was prepared by dissolving of 3M of cyclocarbonate oligomer (3402 g) Laprolate-803 (Example 6) in 2M of isophorondiamine (Creanova specialchemie GmbH) –340 g. This 3742 g were charged into the reactor. The process is as stage 1 (Example 7).

Stage III

The urethane containing oligomer from the stage I was combined with Isophorondiamine (ISPhDA) to form elastomer with Tensile strength 0.7 Mpa and Elongation at break 300%.

EXAMPLE 9

Stage II

"Star" cyclocarbonate oligomer with increased functionality (CCOIF) was used from stage 1 (Example 7) for preparing "star" amino containing hydroxyurethane oligomer with increased functionality (AHUOIF).

AHUOIF was prepared by dissolving of 1M (2438 g) CCOIF from the stage 1 (Example 7) in 8M (1360 g) ISPhDA. The reactor was operated at atmospheric pressure and into several small portions. The reaction is going at 80° C. during 2-3 hours. Total 3798 g. The "star" epoxy oligomer with increased functionality EOIF was prepared by dissolving of 4M (1200 g) of Polypox R-14 (neopentylglycoldiglycidyl ether, UPPC GmbH) in 1M (170 g) of ISPhDA. The reaction is going at 80° C. during 1-2 hours.

Stage III

The urethane containing oligomer AHUOIF and epoxy oligomer EOIF from stage I was combined with 8M (2400 g) Polypox R-14 to form elastomer with Tensile strength 11 Mpa and Elongation at Break 90%.

EXAMPLE 10

Stage II

The AUOIF was used from stage I (Example 9).
The EOIF was used from stage I (Example 9).

Stage III

The urethane containing oligomer HUOIF and epoxy oligomer EOIF from Stage I was combined with 4M (1200 g) of Polypox R-14 to form elastomer with Tensile strength 9 Mpa and Elongation at Break 120%.

A comparison of the network polyurethane properties of examples 7-10 are summarized in the Table 2 of FIG. 8 and compared with the resultant polyurethane obtained using the procedures set forth in U.S. Pat. No. 5,175,312.

EXAMPLE 11

Stage I

An acrylic cyclocarbonate oligomer was prepared using the procedures and equipment of example 1, 425 grams of acrylic epoxy resin Setalux 17-1433 (60%) (Akzo Nobel) was mixed with 0.25% by weight of epoxy of a tetrabutlyammonium bromide catalyst $(C_4H_9)NBr$. The epoxy/catalyst mixture was loaded into the reactor (volume—1 liter). Carbon dioxide was fed under a pressure of 8 bar for 180 minutes. The reaction began at 70° C. and due to the exothermic nature of the reaction ended at a temperature of 120° C.

The reaction resulted in the preparation of 447 grams of an acrylic cyclocarbonate oligomer with 13% cyclocarbonate groups and 0.4% epoxy groups. Conversion was 96%.

Stage II

The amineurethane oligomer with increased functionality (AUOIF) was prepared by dissolving 2M (1170 g) of cyclocarbonate of Polypox R-20 (UPPC) previously synthesized in the reactor using the procedures of Example 6 in 1M (170 g) of Isophorondiamine (Creanova spezialchemie GmbH). The 1340 g mixture of cyclocarbonate in diamine was charged into the reactor, which was jacketed for temperature control. The reaction was conducted at 80° C. for 3 hours, during which an additional 8M (1326 g) of Isophorondiamine was added. The reaction yielded 2700 g of AUOIF.

Stage III

669 g of the acrylic cyclocarbonate oligomer from stage I and 225 g of the AUOIF from stage II were combined by stirring at room temperature to form a liquid that was coated on a metal substrate at a thickness of 50 mkm. The coated substrate was cured for 2 hours at a temperature of 100° C. to form a UV-stable coating. The hardness of the cured coating was H, the impact (face) was 50 kg.cm.

EXAMPLE 12

Stage III

669 g of the acrylic cyclocarbonate oligomer from stage I of Example 11 and 81 g of 100% Vestamine TMD (Creanova) were combined by stirring at room temperature to form a liquid that was coated on a metal substrate at a thickness of 50 mkm. The coated substrate was cured for 2 hours at a temperature of 110° C. to form a UV-stable coating. The hardness of the cured coating was H, the impact (face) was 50 kg.cm.

EXAMPLE 13

Stage II

A synthesis of a cyclocarbonate with a tertiary amine group containing compound was conducted.

A cyclocarbonate based upon Eponex 1510 (Shell) was prepared using the procedures and conditions of Example 6. 562 g of the resultant cyclocarbonate was mixed with 146 grams of N,N-bis(3aminopropyl)methylamine (BASF). The resultant cyclocarbonate/amine mixture was charged into the reactor, which was jacketed for temperature control. The reaction was conducted at 100° C. for a period of 2-3 hours and yielded 708 g of an amino containing oligomer.

Stage III

The 708 g of the amino containing oligomer from stage II and 1340 (100%) acrylic epoxy resin Setalux 17-1433 were combined by stirring at room temperature to form a liquid that was coated on a metal substrate at a thickness of 50 mkm. The coated substrate was cured for 1 hour at a temperature of 100° C. to form a UV-stable coating. The hardness of the cured coating was H, the impact (face) was 50 kg.cm.

The invention claimed is:

1. An improved method of synthesizing a cyclocarbonate from an epoxy compound and carbon dioxide at low pressure and temperature in a reactor, the method comprising the steps of:
    a) supplying a catalyst to the reactor;
    b) introducing the epoxy compound to the catalyst-containing reactor to create a reactionary mass in the reactor; and
    c) feeding carbon dioxide to the reactor
        i) via a first gas inlet into the head space above the reactionary mass, and, substantially simultaneously,
        ii) directly into the reactionary mass through a turbine mixing device comprising a shaft with a hollow interior associated with a gas entrainment impeller directly into the reactionary mass, said shaft having a second gas inlet in fluid communication with the head space and said impeller being in fluid communication with the shaft interior and being positioned within the reactionary mass, said impeller further having peripherally disposed gas dispersion ports suitable for introducing gas into the reactionary mass, whereby
        iii) upon rotation of the shaft and the associated impeller carbon dioxide is drawn into the shaft interior from the head space via the second inlet and is introduced via the dispersion ports into the reactionary mass, the reactionary mass being saturated with the carbon dioxide and reacting to form the cyclocarbonate, said reaction taking place in the absence of reactant solvents and substantially without generation of foam.

2. The method of claim 1, wherein the epoxy compound is selected from the group consisting of aromatic epoxies, aliphatic epoxies, cycloaliphatic epoxies and acrylic epoxies.

3. An apparatus for producing cyclocarbonates from epoxy compounds and carbon dioxide at reduced pressure, time, and temperature, the apparatus comprising:

a) a reactor vessel having an inlet for supplying a catalyst and the epoxy compounds thereto, wherein the catalyst and epoxy compound form a reactionary mass, and a first gas inlet for supplying the carbon dioxide to a head space above the reactionary mass; and
   b) a turbine mixing device located in the reactor vessel, the turbine mixing device comprising a shaft with a hollow interior associated with a gas entrainment impeller, said shaft having a second gas inlet in fluid communication with the head space and said impeller being in fluid communication with the shaft interior and being positioned within the reactionary mass, said impeller further having peripherally disposed gas dispersion ports suitable for introducing gas into the reactionary mass, whereby upon rotation of the shaft and the impeller carbon dioxide is drawn into the shaft interior from the head space via the second inlet and is introduced via the dispersion ports into the reactionary mass.

4. A non-polyester star oligomer selected from the group consisting of star epoxy oligomers having at least three epoxy groups and no more than about 1.0% by weight of terminal cyclocarbonate groups, star cyclocarbonate oligomers having at least three cyclocarbonate groups and no more than about 1.0% by weight of terminal epoxy groups, star hydroxyurethane oligomers having at least three hydroxyurethane groups, and star aminohydroxyurethane oligomers having at least three aminohydroxyurethane groups.

5. The star oligomer of claim 4, wherein said oligomer has a functionality greater than 2.

6. The star hydroxyurethane oligomer according to claim 4, wherein the oligomer comprises at least one hydroxyurethane linkage.

7. The star aminohydroxyurethane oligomer according to claim 4, wherein the oligomer comprises at least one hydroxyurethane linkage.

8. A method of synthesizing a non-polyester star nonisocyanate network polyurethane by cross-linking a star cyclocarbonate having at least three cyclocarbonate groups with a bi-functional amine oligomer having a functionality of at least about 2, at least one of said star cyclocarbonate and said amine oligomer containing a hydroxyurethane linkage.

9. A method of preparing a non-polyester foam star nonisocyanate network polyurethane, comprising the steps of:
   a) cross-linking a star cyclocarbonate with a bi-functional amine oligomer having a functionality of at least about 2; and
   b) adding a blowing agent.

10. The method of claim 9, wherein the blowing agent is pentane.

11. A method of preparing a non-polyester star cyclocarbonate oligomer having at least three cyclocarbonate groups and no more than about 1.0% by weight of terminal epoxy groups, comprising the step of: reacting about x moles of a primary diamine with about y moles of a cyclocarbonate oligomer in at least one step to form a star cyclocarbonate oligomer of increased functionality, wherein $X \geq 1$, $y \geq 2$, $y > x$.

12. The method of claim 11, wherein the primary diamine is selected from the group consisting of substantially linear aliphatic primary diamines, primary diamines comprising alicyclic groups, and mixtures thereof.

13. A method of preparing a non-polyester star epoxy oligomer having at least three epoxy groups and no more than about 1.0% by weight of terminal cyclocarbonate groups, comprising the step of: reacting a total of about x moles of a primary diamine with y moles of an epoxy oligomer in at least one step to form a star epoxy oligomer of increased functionality, wherein $x \geq 1$, $y \geq 2$, $y > x$.

14. The method of claim 13, wherein the primary diamine is selected from the group consisting of substantially linear aliphatic primary diamines, primary diamines comprising alicyclic groups, and mixtures thereof.

15. A method of preparing a non-polyester star aminohydroxyurethane oligomer having at least three aminohydroxyurethane groups, comprising the step of: reacting a star cyclocarbonate oligomer having at least three cyclocarbonate groups and a hydroxyurethane linkage with a primary diamine.

16. The method of claim 15, wherein the primary diamine is selected from the group consisting of substantially linear aliphatic primary diamines, primary diamines comprising alicyclic groups, and mixtures thereof.

17. A method of synthesizing a non-polyester acrylic nonisocyanate network polyurethane by cross-linking an acrylic cyclocarbonate having at least three cyclocarbonate groups with a bi-functional amine oligomer having a functionality of at least about 2.

18. A method of preparing a non-polyester foam acrylic nonisocyanate network polyurethane comprising the steps of:
   a) cross-linking an acrylic cyclocarbonate having at least three cyclocarbonate groups with a bi-functional amine oligomer having a functionality of at least about 2; and
   b) adding a blowing agent.

19. The method of claim 18, wherein the blowing agent is pentane.

20. A method of preparing a non-polyester acrylic cyclocarbonate oligomer having at least three cyclocarbonate groups, comprising the step of: reacting an acrylic epoxy resin with carbon dioxide in the presence of a catalyst.

21. A method of preparing a non-polyester acrylic aminohydroxyurethane oligomer comprising the step of: reacting an acrylic cyclocarbonate oligomer having at least three cyclocarbonate groups with a primary diamine.

22. The method of claim 21, wherein the primary diamine is selected from the group consisting of substantially linear aliphatic primary diamines, primary diamines comprising alicyclic groups, and mixtures thereof.

23. A non-polyester star noniso-cyanate network polyurethane in the form of a foam or a UV stable coating.

Figure 9:
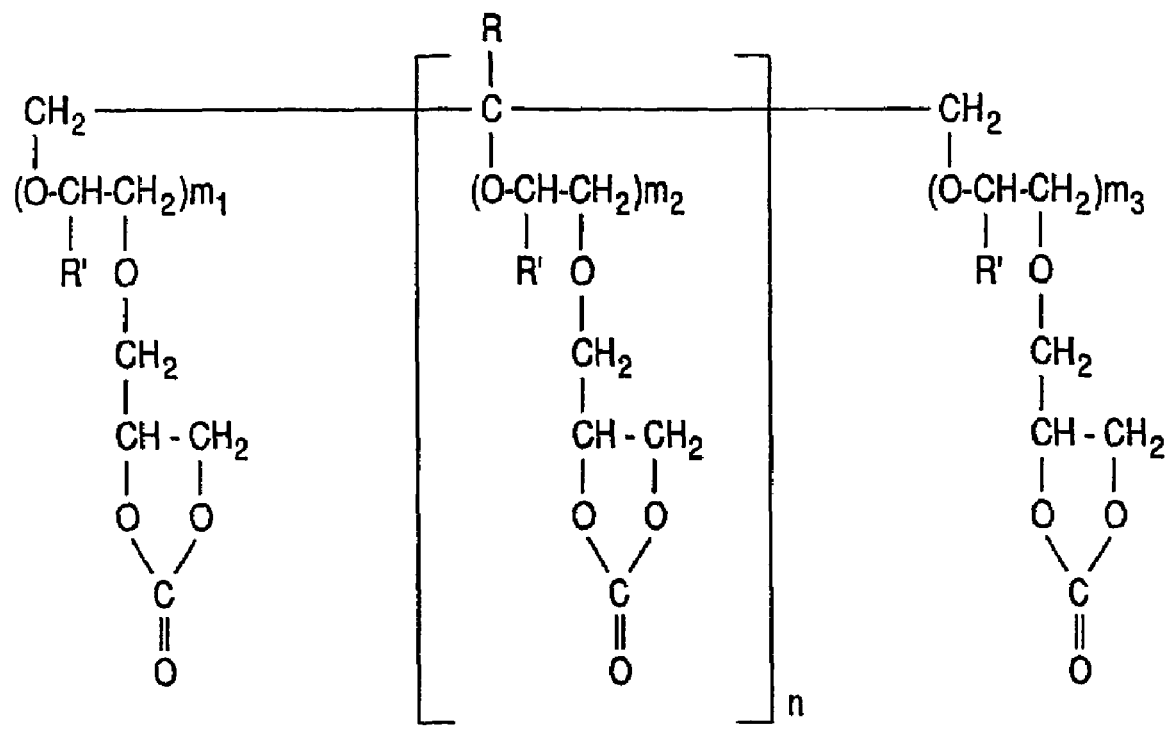
FIG. 9 depicts the formula for a reactant used to make a cyclocarbonate terminated "star" oligomer of increased functionality.

24. A method of preparing a non-polyester star cyclocarbonate oligomer having no more than about 1.0% by weight of terminal epoxy groups by reacting about 1 to about 2 moles of primary diamine with about 2 to about 3 moles of the compound of the formula depicted in FIG. 9, wherein $R=H$, $CH_3$ or $C_2H_5$, $R'=CH_2Cl$ or $CH_3$, $n=1, 2$ or $3$, and m1, m2 and m3 are independently selected over the range from 3 to 12 inclusive such that the molecular weight of the star cyclocarbonate oligomer is about 600-1600.

25. A non-polyester acrylic nonisocyanate network polyurethane in the form of a foam or a UV stable coating.

26. The method of claim 1, wherein the reaction is completed within a period of about 40-120 minutes.

* * * * *

UNITED STATES PATENT AND TRADEMARK OFFICE
CERTIFICATE OF CORRECTION

PATENT NO. : 7,232,877 B2
APPLICATION NO. : 10/491268
DATED : June 19, 2007
INVENTOR(S) : Oleg Figovsky and Leonid Shapovalov It is certified that error appears in the above-identified patent and that said Letters Patent is hereby corrected as shown below:

Title page, Item (54), third line: "IONISOCYANATE" should read -- NONISOCYANATE --.

Column 1, line 3: "IONISOCYANATE" should read -- NONISOCYANATE --.

Column 2, line 9: "hydrogenated" should read -- hydrogen --.

Column 4, line 7, after "reaction of an" delete [epoxy or].

Signed and Sealed this

Twenty-sixth Day of February, 2008

JON W. DUDAS
*Director of the United States Patent and Trademark Office*